United States Patent
Ma et al.

(10) Patent No.: US 9,818,320 B2
(45) Date of Patent: Nov. 14, 2017

(54) DEVICE AND METHOD FOR TESTING TRANSPARENCY EFFECT OF TRANSPARENT DISPLAY SUBSTRATE USING A REFERENCE OBJECT WITH TWO KINDS OF REGIONS OF DIFFERENT COLORS

(71) Applicant: BOE TECHNOLOGY GROUP CO., LTD., Beijing (CN)

(72) Inventors: Xinli Ma, Beijing (CN); Hangman Lai, Beijing (CN)

(73) Assignee: BOE TECHNOLOGY GROUP CO., LTD., Beijing (CN)

(*) Notice: Subject to any disclaimer, the term of this patent is extended or adjusted under 35 U.S.C. 154(b) by 112 days.

(21) Appl. No.: 14/913,560

(22) PCT Filed: Sep. 18, 2015

(86) PCT No.: PCT/CN2015/089914
§ 371 (c)(1),
(2) Date: Feb. 22, 2016

(87) PCT Pub. No.: WO2016/183987
PCT Pub. Date: Nov. 24, 2016

(65) Prior Publication Data
US 2017/0162090 A1    Jun. 8, 2017

(30) Foreign Application Priority Data

May 18, 2015  (CN) .......................... 2015 1 0254560

(51) Int. Cl.
*G01J 1/42* (2006.01)
*G09G 3/00* (2006.01)
*G01M 11/00* (2006.01)

(52) U.S. Cl.
CPC ............... *G09G 3/006* (2013.01); *G01J 1/42* (2013.01); *G01M 11/00* (2013.01); *G09G 2320/0646* (2013.01); *G09G 2320/0666* (2013.01)

(58) Field of Classification Search
CPC ...... G01J 1/42; G01M 11/00; G01M 11/0235; G01B 11/0625
(Continued)

(56) References Cited

U.S. PATENT DOCUMENTS 9,530,337 B2* 12/2016 Hu .................. G09G 3/006

FOREIGN PATENT DOCUMENTS

| CN | 101320466 | 12/2008 |
| CN | 101320466 A | 12/2008 |

(Continued)

OTHER PUBLICATIONS

Written Opinion of the International Searching Authority from PCT Application No. PCT/CN2015/089914, dated Jan. 18, 2016 (4 pages).

(Continued)

*Primary Examiner* — Que T Le
(74) *Attorney, Agent, or Firm* — Harness, Dickey & Pierce, P.L.C.

(57) ABSTRACT

Embodiments of the present invention provide a device and a method for testing transparency effect of a transparent display substrate. The device comprises a transparency identification module, an optical measurement unit and a reference object including two kinds of regions of different colors. The optical measurement unit is able to directly measure brightness of the two kinds of regions of different colors of the reference object to acquire a first brightness difference, and to measure brightness of the two kinds of (Continued)

regions of different colors of the reference object through the transparent display substrate to acquire a second brightness difference. Based on the first brightness difference and the second brightness difference, the transparency identification module calculates identification degree ID of the transparent display substrate according to the equation:

$$ID = \frac{\Delta L_2}{\Delta L_1} \times 100\%,$$

where $\Delta L_1$ is the first brightness difference and $\Delta L_2$ is the second brightness difference. Embodiments of the present invention may eliminate the influence of ambient light on the test and increase the test accuracy of the transparent display substrate.

20 Claims, 4 Drawing Sheets

(58) Field of Classification Search
USPC .................................. 250/559.4, 221, 216
See application file for complete search history.

(56) References Cited

FOREIGN PATENT DOCUMENTS

| | | |
|---|---|---|
| CN | 101660968 A | 3/2010 |
| CN | 102928442 A | 2/2013 |
| CN | 102967443 | 3/2013 |
| CN | 102967443 A | 3/2013 |
| CN | 202916071 | 5/2013 |
| CN | 202916071 U | 5/2013 |
| CN | 103900795 | 7/2014 |
| CN | 103900795 A | 7/2014 |
| CN | 104165753 A | 11/2014 |
| EP | 2239552 | 10/2010 |
| JP | 2264849 | 10/1990 |
| JP | H02264849 A | 10/1990 |
| KR | 101485253 B1 | 1/2015 |

OTHER PUBLICATIONS

Office Action from corresponding Chinese Application No. 201510254560.4, dated Mar. 1, 2017 (8 pages).

\* cited by examiner

DEVICE AND METHOD FOR TESTING TRANSPARENCY EFFECT OF TRANSPARENT DISPLAY SUBSTRATE USING A REFERENCE OBJECT WITH TWO KINDS OF REGIONS OF DIFFERENT COLORS

TECHNICAL FIELD

Embodiments of the present invention relate to a device and a method for testing transparency effect of a transparent display substrate.

BACKGROUND

At present, with the developments of display technologies, transparent display technology as an emerging display technology has got more and more attention. When a transparent display substrate displays an image, the user can, through the transparent display substrate, see an object placed therebehind. The better the transparency effect is, the clearer the object behind the transparent display substrate is seen by the user through the transparent display substrate. Therefore, the test on the transparency effect of the transparent display substrate has become especially important.

In prior art, the following two methods are generally employed to test a transparent display substrate with a transparency effect measurement apparatus (see FIG. 1). In the first method, a test plate including black and white patterns is placed behind a transparent display substrate. Brightness $L_B$ of the black regions and brightness $L_W$ of the white regions in the test plate is detected through the transparent display substrate respectively by using a display color analyzer CA210. A brightness contrast parameter T between the black regions and white regions in the test plate is acquired based on the brightness $L_B$ of the black regions and the brightness $L_W$ of the white regions as well as the equation $$T = \frac{L_W}{L_B} \times 100\%.$$

The transparency effect of the transparent display substrate is determined according to the brightness contrast parameter T, wherein the greater the brightness contrast parameter T is, the better the transparency effect of the transparent display substrate is. In the second method, firstly, brightness of the black regions and brightness of the white regions in the test plate are directly detected to acquire an initial contrast parameter $T_0$. Then, a contrast parameter T between brightness of the black regions and brightness of the white regions is acquired through the transparent display substrate. A transparency effect parameter CR of the transparent display substrate is acquired based on the contrast parameter T and the initial contrast parameter $T_0$ as well as the equation $$CR = \frac{T_1}{T_0} \times 100\%.$$

The transparency effect of the transparent display substrate is determined according to the transparency effect parameter CR, wherein the greater the transparency effect parameter CR is, the better the transparency effect of the transparent display substrate is.

However, no matter which one of the above methods is employed to test the transparent display substrate, the test has to be performed under a certain illumination condition. Therefore, the test will be inevitably disturbed by ambient light, and the test accuracy of the transparent display substrate is thereby influenced.

SUMMARY

Embodiments of the present invention can, inter alia, solve the problem of poor test accuracy of the transparency effect of a transparent display substrate caused by the disturbance of ambient light in prior art.

An embodiment of the present invention provides a device for testing transparency effect of a transparent display substrate, comprising: a transparency identification module, an optical measurement unit and a reference object including two kinds of regions of different colors. The optical measurement unit is able to directly measure brightness of the two kinds of regions of different colors of the reference object to acquire a first brightness difference, and to measure brightness of the two kinds of regions of different colors of the reference object through the transparent display substrate to acquire a second brightness difference. Based on the first brightness difference and the second brightness difference, the transparency identification module calculates identification degree ID of the transparent display substrate according to the equation:

$$ID = \frac{\Delta L_2}{\Delta L_1} \times 100\%,$$

where $\Delta L_1$ is the first brightness difference and $\Delta L_2$ is the second brightness difference.

The device for testing transparency effect of a transparent display substrate according to the embodiment of the present invention comprises the transparency identification module, the optical measurement unit and the reference object. When the device is used to test the transparency of the transparent display substrate, the first brightness difference may be directly acquired by means of the optical measurement unit and the reference object, and the brightness of the two kinds of regions of different colors of the reference object may be measured through the transparent display substrate to acquire the second brightness difference. The identification degree of the reference object may be calculated according to the first brightness difference and the second brightness difference. Because the transparency effect of the transparent display substrate has a direct influence on whether an object behind the transparent display substrate can be clearly seen through the transparent display substrate, and the identification degree of the object is an important factor for measuring whether the object behind the transparent display substrate can be clearly seen, the transparency effect of the transparent display substrate may be determined by measuring the influence of the transparent display substrate on the identification degree of the reference object, thereby achieving the objective of testing the transparency effect of the transparent display substrate, which is advantageous for testing the transparent display substrate. Furthermore, because the influences of ambient light on different portions of the reference object are the same, acquiring the identification degree by means of the brightness differences may eliminate the influence of ambient light on the test and increase the test accuracy of the transparent display substrate.

Optionally, distance between the optical measurement unit and the reference object is fixed.

Because the distance between the optical measurement unit and the reference object may influence the identification degree of the reference object measured by using the optical measurement unit, in order to test the transparency effect of the transparent display substrate more accurately, the distance between the optical measurement unit and the reference object may be fixed. After the optical measurement unit is used to directly measure the brightness of the reference object, the transparent display substrate may be placed between the optical measurement unit and the reference object, and the identification degree of the reference object may be measured through the transparent display substrate, thereby preventing the measurement result from being influenced by unfixed distance between the optical measurement unit and the reference object, which is advantageous for accurately determining the influence of the transparent display substrate on the identification degree of the reference object, thereby testing the transparency effect of the transparent display substrate more accurately.

Optionally, the optical measurement unit is a brightness meter or an image sensor.

Because different regions on the reference object may be measured by means of a brightness meter or an image sensor, the result measured by using a brightness meter or an image sensor may reflect the identification degree of the reference object more comprehensively, which is thereby advantageous for determining the transparency effect of the transparent display substrate more accurately.

Optionally, the reference object is a standard color plate comprising black regions spaced from each other and white regions spaced from each other.

Because the standard color plate has a simple structure, and the black regions and white regions of the standard color plate are of standard colors, using a standard color plate as the reference object is advantageous for increasing the accuracy of the identification degree test.

Optionally, when the optical measurement unit directly measures the brightness of the reference object, the difference value between the brightness of the white regions and the brightness of the black regions is the first brightness difference; and when the optical measurement unit measures the brightness of the reference object through the transparent display substrate, the difference value between the brightness of the white regions and the brightness of the black regions is the second brightness difference.

Optionally, the device further comprises a light source, and the distance and angle between the light source and the reference object are both fixed.

Stable and continuous illumination may be provided for the reference object during the process of the test by means of the light source, which is advantageous for the test of the transparency effect. Furthermore, because the distance and angle between the light source and the reference object may both influence the illuminance on the surface of the reference object, thereby influencing the identification degree of the reference object measured by using the optical measurement unit, the distance and angle between the light source and the reference object may both be fixed, so as to prevent the measurement result from being influenced by the distance and angle between the light source and the reference object. This is advantageous for accurately determining the influence of the transparent display substrate on the identification degree of the reference object, thereby testing the transparency effect of the transparent display substrate more accurately.

Optionally, when the brightness of the reference object is measured through the transparent display substrate, the light source and the reference object are located at the same side of the transparent display substrate.

By locating the light source and the reference object at the same side of the transparent display substrate when the brightness of the reference object is measured through the transparent display substrate, the illumination effect of the light source on the reference object may be enhanced, which is advantageous for the test of the transparency effect thereby increasing the test accuracy of the transparency effect.

An embodiment of the present invention provides a method for testing transparency effect of a transparent display substrate, comprising:

selecting a reference object including two kinds of regions of different colors;

using an optical measurement unit to directly measure brightness of the two kinds of regions of different colors of the reference object to acquire a first brightness difference $\Delta L_1$;

placing the transparent display substrate between the optical measurement unit and the reference object, and using the optical measurement unit to measure brightness of the two kinds of regions of different colors of the reference object through the transparent display substrate to acquire a second brightness difference $\Delta L_2$;

based on the first brightness difference and the second brightness difference, calculating identification degree ID of the transparent display substrate by a transparency identification module according to the equation:

$$ID = \frac{\Delta L_2}{\Delta L_1} \times 100\%;$$

and determining the transparency effect of the transparent display substrate according to the identification degree ID. Specifically, the higher the identification degree ID is, the better the transparency effect is.

In the method for testing transparency effect of a transparent display substrate according to the embodiment of the present invention, the first brightness difference is directly acquired by means of the optical measurement unit and the reference object, and the brightness of the two kinds of regions of different colors of the reference object is measured through the transparent display substrate to acquire the second brightness difference. The identification degree of the reference object may be calculated according to the first brightness difference and the second brightness difference. Because the transparency effect of the transparent display substrate has a direct influence on whether an object behind the transparent display substrate can be clearly seen through the transparent display substrate, and the identification degree of the object is an important factor for measuring whether the object behind the transparent display substrate can be clearly seen, the transparency effect of the transparent display substrate may be determined by measuring the influence of the transparent display substrate on the identification degree of the reference object, thereby achieving the objective of testing the transparency effect of the transparent display substrate, which is advantageous for testing the transparent display substrate. Furthermore, because the influences of ambient light on different portions of the reference object are the same, acquiring the identification degree by means of the brightness differences may eliminate the influence of ambient light on the test and increase the test accuracy of the transparent display substrate.

Optionally, the reference object is a standard color plate comprising black regions spaced from each other and white regions spaced from each other.

Because the standard color plate has a simple structure, and the black regions and white regions of the standard color plate are of standard colors, using a standard color plate as the reference object is advantageous for increasing the accuracy of the identification degree test.

Optionally, when the optical measurement unit directly measures the brightness of the reference object, the difference value between the brightness of the white regions and the brightness of the black regions is the first brightness difference; and when the optical measurement unit measures the brightness of the reference object through the transparent display substrate, the difference value between the brightness of the white regions and the brightness of the black regions is the second brightness difference.

Optionally, using the optical measurement unit to directly measure the reference object to acquire the first brightness difference $\Delta L_1$ comprises:
respectively measuring brightness of different portions of the black regions and brightness of different portions of the white regions, and drawing a brightness curve according to the measured respective brightness values;
calculating brightness of the black regions and brightness of the white regions, wherein the brightness of the black regions is an average value of respective brightness values of wave trough portions of the brightness curve, and the brightness of the white regions is an average value of respective brightness values of wave peak portions of the brightness curve; and
calculating a difference value between the brightness of the white regions and the brightness of the black regions as the first brightness difference $\Delta L_1$.

Due to the influence of various external factors, the brightness values of different portions of the black regions may be different from each other, and the brightness values of different portions of the white regions may also be different from each other. As a consequence, the test accuracy of the transparency effect may be increased by taking the average value of respective brightness values of wave trough portions as the brightness of the black regions and taking the average value of respective brightness values of wave peak portions as the brightness of the white regions.

Optionally, calculating the brightness of the black regions and the brightness of the white regions comprises:
in respective brightness values located at the wave trough portions of the brightness curve, taking 110% of a minimum value of the respective brightness values as a minimum brightness value, to calculate the average value of the respective brightness values located at the wave trough portions; and
in respective brightness values located at the wave peak portions of the brightness curve, taking 90% of a maximum value of the respective brightness values as a maximum brightness value, to calculate the average value of the respective brightness values located at the wave peak portions.

By taking 110% of the minimum value of respective brightness values of the wave trough portions of the brightness curve as the minimum brightness value and taking 90% of the maximum value of respective brightness values of the wave peak portions of the brightness curve as the maximum brightness value to make certain modifications to the measured brightness values, the occurrence of extreme values may be effectively avoided thereby further increasing the test accuracy.

Optionally, using the optical measurement unit to measure the brightness of the two kinds of regions of different colors of the reference object through the transparent display substrate to acquire the second brightness difference $\Delta L_2$ comprises:
using the optical measurement unit to respectively measure brightness of different portions of the black regions and brightness of different portions of the white regions through the transparent display substrate, and drawing a brightness curve according to the measured respective brightness values;
calculating brightness of the black regions and brightness of the white regions, wherein the brightness of the black regions is an average value of respective brightness values of wave trough portions of the brightness curve, and the brightness of the white regions is an average value of respective brightness values of wave peak portions of the brightness curve; and
calculating a difference value between the brightness of the white regions and the brightness of the black regions as the second brightness difference $\Delta L_2$.

Optionally, calculating the brightness of the black regions and the brightness of the white regions comprises:
in respective brightness values located at the wave trough portions of the brightness curve, taking 110% of a minimum value of the respective brightness values as a minimum brightness value, to calculate the average value of the respective brightness values located at the wave trough portions; and
in respective brightness values located at the wave peak portions of the brightness curve, taking 90% of a maximum value of the respective brightness values as a maximum brightness value, to calculate the average value of the respective brightness values located at the wave peak portions.

BRIEF DESCRIPTION OF THE DRAWINGS

In order to illustrate the technical solutions of embodiments of the present invention more clearly, the drawings of embodiments will be introduced briefly below. Apparently, the drawings in the following description relate merely to some embodiments of the present invention, but should not be construed as limiting the present invention.

DETAILED DESCRIPTION

In order to make the objectives, technical solutions and advantages of embodiments of the present invention apparent, the technical solutions of embodiments of the present invention will be described clearly and completely hereinafter in conjunction with the drawings of embodiments of the present invention. Apparently, embodiments described herein are merely a part of but not all embodiments of the present invention. Based on embodiments of the present invention described herein, those skilled in the art can obtain other embodiments without any creative work, which should be within the scope of the present invention.

Embodiments of the present invention provide a device and a method for testing transparency effect of a transparent display substrate. Hereinafter, two embodiments will be provided respectively to illustrate the device and method for testing transparency effect of a transparent display substrate according to embodiments of the present invention.

Figure 1:
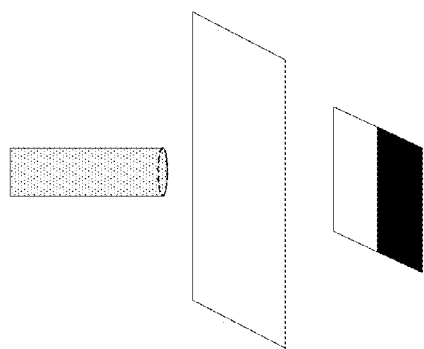
FIG. 1 is a structural schematic diagram of a device for testing transparency of a transparent display substrate in prior art.
Figure 2:
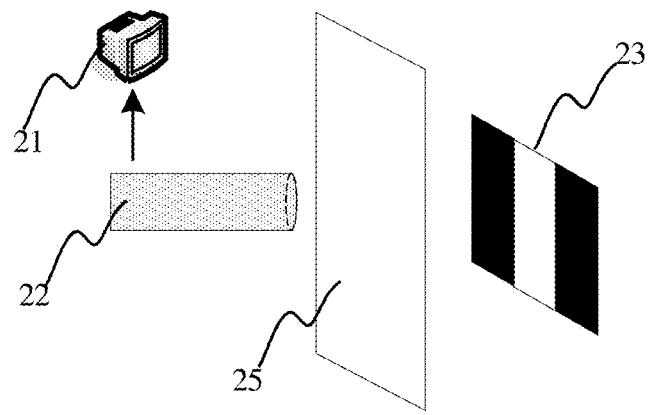
FIG. 2 is a structural schematic diagram of a device for testing transparency of a transparent display substrate according to the first embodiment of the present invention.

The first embodiment of the present invention provides a device for testing transparency effect of a transparent display substrate. With reference to FIG. 2, the device comprises: a transparency identification module 21, an optical measurement unit 22 and a reference object 23 including two kinds of regions of different colors. The optical measurement unit 22 is able to directly measure brightness of the two kinds of regions of different colors of the reference object 23 to acquire a first brightness difference, and to measure brightness of the two kinds of regions of different colors of the reference object 23 through the transparent display substrate 25 to acquire a second brightness difference. Based on the first brightness difference and the second brightness difference, the transparency identification module calculates identification degree ID of the transparent display substrate according to the equation:

$$ID = \frac{\Delta L_2}{\Delta L_1} \times 100\%,$$

where $\Delta L_1$ is the first brightness difference and $\Delta L_2$ is the second brightness difference.

In the device for testing transparency effect of a transparent display substrate according to the first embodiment of the present invention, when the device is used to test the transparency of the transparent display substrate, firstly, the first brightness difference is directly acquired by means of the optical measurement unit and the reference object, and the brightness of the two kinds of regions of different colors of the reference object is measured through the transparent display substrate to acquire the second brightness difference. The identification degree of the reference object may be calculated according to the first brightness difference and the second brightness difference. Because the transparency effect of the transparent display substrate has a direct influence on whether an object behind the transparent display substrate can be clearly seen through the transparent display substrate, and the identification degree of the object is an important factor for measuring whether the object behind the transparent display substrate can be clearly seen, the transparency effect of the transparent display substrate may be determined by measuring the influence of the transparent display substrate on the identification degree of the reference object, thereby achieving the objective of testing the transparency effect of the transparent display substrate, which is advantageous for testing the transparent display substrate. Furthermore, because the influences of ambient light on different portions of the reference object are the same, acquiring the identification degree by means of the brightness differences may eliminate the influence of ambient light on the test and increase the test accuracy of the transparent display substrate.

Optionally, distance between the optical measurement unit 22 and the reference object 23 is fixed.

Because the distance between the optical measurement unit and the reference object may influence the identification degree of the reference object measured by using the optical measurement unit, in order to test the transparency effect of the transparent display substrate more accurately, the distance between the optical measurement unit and the reference object may be fixed. After the optical measurement unit is used to directly measure the brightness of the reference object, the transparent display substrate may be placed between the optical measurement unit and the reference object, and the identification degree of the reference object may be measured through the transparent display substrate, thereby preventing the measurement result from being influenced by unfixed distance between the optical measurement unit and the reference object, which is advantageous for accurately determining the influence of the transparent display substrate on the identification degree of the reference object, thereby testing the transparency effect of the transparent display substrate more accurately.

Optionally, the optical measurement unit 22 is a brightness meter or an image sensor.

Because different regions on the reference object may be measured by means of a brightness meter or an image sensor, the result measured by using a brightness meter or an image sensor in the embodiment of the present invention may reflect the identification degree of the reference object more comprehensively, which is thereby advantageous for determining the transparency effect of the transparent display substrate more accurately. The optical measurement unit 22 may be a brightness meter or an image sensor, or may be any other brightness measurement instrument which can reflect the identification degree of the reference object comprehensively.

Optionally, with reference to FIG. 2, the reference object 23 is a standard color plate comprising black regions spaced from each other and white regions spaced from each other.

Because the standard color plate has a simple structure, and the black regions and white regions of the standard color plate are of standard colors, using a standard color plate as the reference object is advantageous for increasing the accuracy of the identification degree test.

Further, the reference object may also be a liquid crystal display device. However, when a liquid crystal display device is used as the reference object, it is required to configure the liquid crystal display device as black patterns and white patterns. Because special adjustments are required when the liquid crystal display device is configured as black patterns and white patterns, the process is relatively complicated. Furthermore, due to the influence of display effect of the liquid crystal display device itself, the black patterns and white patterns can hardly achieve standard black and white. Moreover, the reference object may also be any other display devices such as an Organic Light Emitting Diode (OLED) display device, a Plasma Display Panel (PDP) display device, or a Cathode Ray Tube (CRT) display device.

In the case where the standard color plate is used as the reference object, when the optical measurement unit 22 directly measures brightness of the reference object 23, the difference value between the brightness of the white regions and the brightness of the black regions is the first brightness difference $\Delta L_1$; when the optical measurement unit 22 measures brightness of the reference object 23 through the transparent display substrate 25, the difference value between the brightness of the white regions and the brightness of the black regions is the second brightness difference $\Delta L_2$.

When the optical measurement unit 22 is used to directly measure brightness of the reference object 23, brightness of different portions of the black regions B and brightness of different portions of the white regions W are measured respectively, and a brightness curve is drawn according to the measured respective brightness values, wherein the brightness of the black regions is an average value of respective brightness values of wave trough portions of the brightness curve, and the brightness of the white regions is an average value of respective brightness values of wave peak portions of the brightness curve. Due to the influence of various external factors such as manufacturing technology level, measurement error and environmental factors, the measured brightness values of different portions of the black regions may be different from each other, and the measured brightness values of different portions of the white regions may also be different from each other. As a consequence, the test accuracy of the transparency effect may be increased in the embodiment of the present invention by taking the average value of respective brightness values of wave trough portions as the brightness of the black regions and taking the average value of respective brightness values of wave peak portions as the brightness of the white regions.

Optionally, 110% of a minimum value of respective brightness values of wave trough portions of the brightness curve may be taken as a minimum brightness value, and 90% of a maximum value of respective brightness values of wave peak portions of the brightness curve may be taken as a maximum brightness value. By making certain modifications to the measured brightness values in such a way, the occurrence of extreme values may be avoided thereby further increasing the test accuracy.

Optionally, illuminance on the standard color plate is fixed. When the illuminance on the standard color plate is fixed, comparison and determination of transparency effects of different transparent display substrates can be facilitated.

Figure 3:
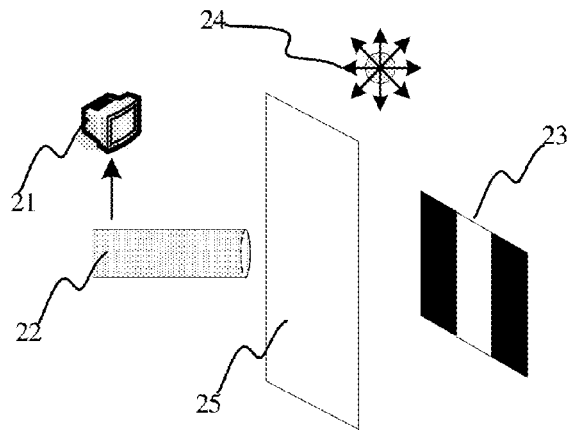
FIG. 3 is a structural schematic diagram of a device for testing transparency of a transparent display substrate according to the second embodiment of the present invention.

The second embodiment of the present invention provides a device for testing transparency effect of a transparent display substrate. With reference to FIG. 3, compared with the device for testing transparency effect of a transparent display substrate according to the first embodiment of the present invention, the device for testing transparency effect of a transparent display substrate according to the second embodiment of the present invention further comprises a light source 24. By providing stable and continuous illumination for the test process by means of the light source 24, the influence of natural light on the test result may be decreased so as to further increase the test accuracy of the transparency effect.

Optionally, the light source 24 is a standard light source. In addition, the light source may also be an ordinary light source. However, relative to an ordinary light source, a standard light source generally complies with international standards, and the illumination it provides is more stable and easier for adjustment. Therefore, a standard light source (e.g., a D65 standard light source) is generally selected as the light source 24.

Optionally, the distance and angle between the light source 24 and the reference object 23 are both fixed. Because the distance and angle between the light source 24 and the reference object 23 may both influence the illuminance on the surface of the reference object, thereby influencing the identification degree of the reference object measured by using the optical measurement unit, the distance and angle between the light source and the reference object may both be fixed, so as to prevent the measurement result from being influenced by the distance and angle between the light source and the reference object. This is advantageous for accurately determining the influence of the transparent display substrate on the identification degree of the reference object, thereby testing the transparency effect of the transparent display substrate more accurately.

Figure 4:
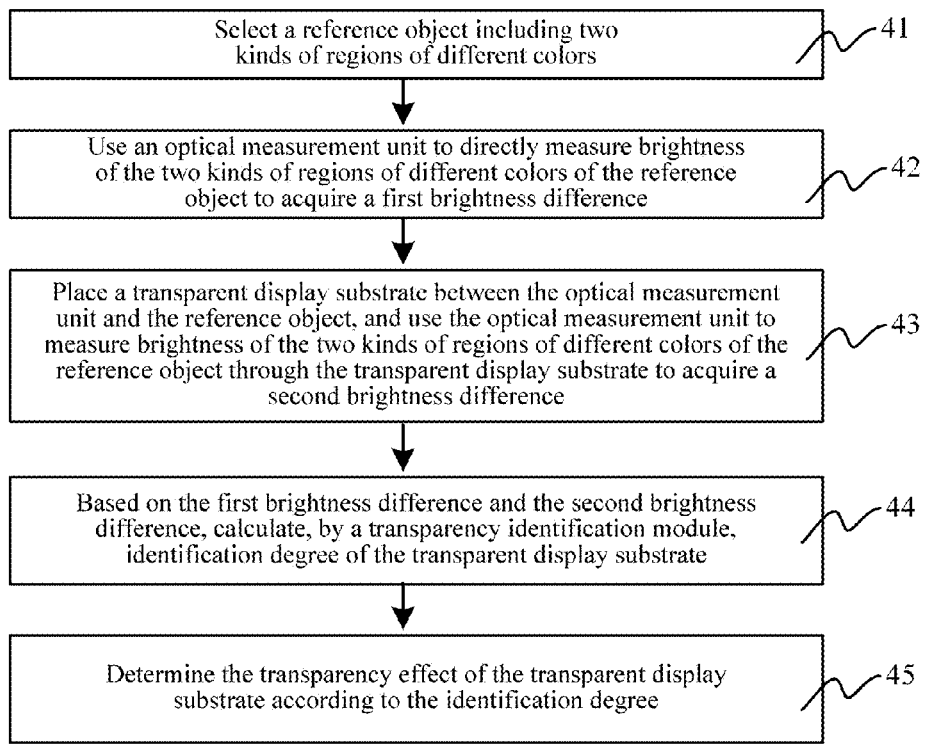
FIG. 4 is a flow chart of a method for testing transparency effect of a transparent display substrate according to the third embodiment of the present invention.

The third embodiment of the present invention provides a method for testing transparency effect of a transparent display substrate. With reference to FIG. 4, the method comprises:

step 41 of selecting a reference object including two kinds of regions of different colors; step 42 of using an optical measurement unit to directly measure brightness of the two kinds of regions of different colors of the reference object to acquire a first brightness difference $\Delta L_1$;

step 43 of placing the transparent display substrate between the optical measurement unit and the reference object, and using the optical measurement unit to measure brightness of the two kinds of regions of different colors of the reference object through the transparent display substrate to acquire a second brightness difference $\Delta L_2$;

step 44 of calculating, by a transparency identification module, identification degree ID of the transparent display substrate, based on the first brightness difference and the second brightness difference according to the equation:

$$ID = \frac{\Delta L_2}{\Delta L_1} \times 100\%;$$

and step 45 of determining the transparency effect of the transparent display substrate according to the identification degree ID. Specifically, the higher the identification degree ID is, the better the transparency effect is.

In the method for testing transparency effect of a transparent display substrate according to the third embodiment of the present invention, the first brightness difference is directly acquired by means of the optical measurement unit and the reference object, and the brightness of the two kinds of regions of different colors of the reference object is measured through the transparent display substrate to acquire the second brightness difference. The identification degree of the reference object may be calculated according to the first brightness difference and the second brightness difference. Because the transparency effect of the transparent display substrate has a direct influence on whether an object behind the transparent display substrate can be clearly seen through the transparent display substrate, and the identification degree of the object is an important factor for measuring whether the object behind the transparent display substrate can be clearly seen, the transparency effect of the transparent display substrate may be determined by measuring the influence of the transparent display substrate on the identification degree of the reference object, thereby achieving the objective of testing the transparency effect of the transparent display substrate, which is advantageous for testing the transparent display substrate. Furthermore, because the influences of ambient light on different portions of the reference object are the same, acquiring the identification degree by means of the brightness differences may eliminate the influence of ambient light on the test and increase the test accuracy of the transparent display substrate.

Optionally, the reference object 23 is a standard color plate comprising black regions spaced from each other and white regions spaced from each other.

Because the standard color plate has a simple structure, and the black regions and white regions of the standard color plate are of standard colors, using a standard color plate as the reference object is advantageous for increasing the accuracy of the identification degree test.

Further, the reference object may also be any other display such as a liquid crystal display, an Organic Light Emitting Diode (OLED) display, a Plasma Display Panel (PDP) display, or a Cathode Ray Tube (CRT) display. However, when a display device such as a liquid crystal display is used as the reference object, it is required to configure the liquid crystal display as black patterns and white patterns. Because special adjustments are required when the liquid crystal display is configured as black patterns and white patterns, the process is relatively complicated. Furthermore, due to the influence of display effect of the liquid crystal display itself, the black patterns and white patterns can hardly achieve standard black and white.

In the case where the standard color plate is used as the reference object, when the optical measurement unit directly measures brightness of the reference object, the difference value between the brightness of the white regions and the brightness of the black regions is the first brightness difference $\Delta L_1$; when the optical measurement unit measures brightness of the reference object through the transparent display substrate, the difference value between the brightness of the white regions and the brightness of the black regions is the second brightness difference $\Delta L_2$.

Figure 5:
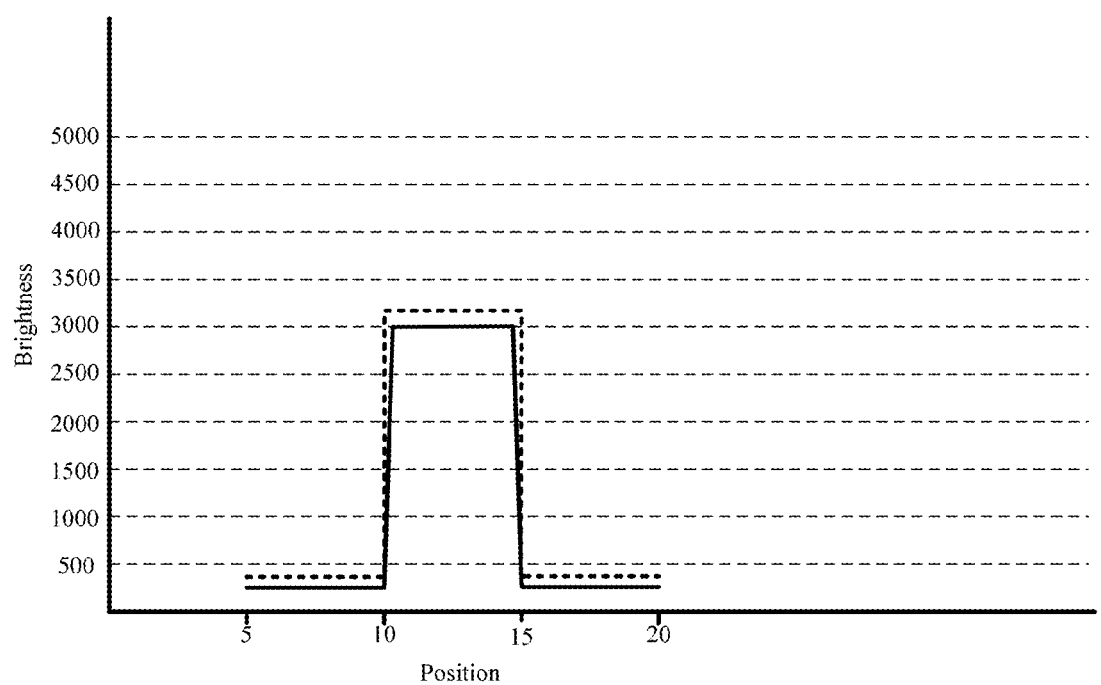
FIG. 5 is a schematic diagram of a brightness curve drawn based on the measured respective brightness values of different portions of the reference object, according to the third embodiment of the present invention.

Optionally, using the optical measurement unit to directly measure the reference object to acquire the first brightness difference $\Delta L_1$ comprises:
respectively measuring brightness of different portions of the black regions and brightness of different portions of the white regions, and drawing a brightness curve according to the measured respective brightness values, as shown in FIG. 5 (see the dashed line);
calculating brightness $L_B^1$ of the black regions and brightness $L_W^1$ of the white regions, wherein the brightness $L_B^1$ of the black regions is an average value of respective brightness values of wave trough portions of the brightness curve, and the brightness $L_W^1$ of the white regions is an average value of respective brightness values of wave peak portions of the brightness curve; and
calculating a difference value between the brightness $L_W^1$ of the white regions and the brightness $L_B^1$ of the black regions as the first brightness difference $\Delta L_1$ according to the equation:

$$\Delta L_1 = L_W^1 - L_B^1,$$

where $L_W^1$ is the brightness of the white regions and $L_B^1$ is the brightness of the black regions.

Due to the influence of various external factors, the brightness values of different portions of the black regions may be different from each other, and the brightness values of different portions of the white regions may also be different from each other. As a consequence, the test accuracy of the transparency effect may be increased by taking the average value of respective brightness values of wave trough portions as the brightness of the black regions and taking the average value of respective brightness values of wave peak portions as the brightness of the white regions.

Optionally, calculating the brightness of the black regions and the brightness of the white regions comprises:
in respective brightness values located at the wave trough portions of the brightness curve, taking 110% of a minimum value of the respective brightness values as a minimum brightness value, to calculate the average value of the respective brightness values located at the wave trough portions; and
in respective brightness values located at the wave peak portions of the brightness curve, taking 90% of a maximum value of the respective brightness values as a maximum brightness value, to calculate the average value of the respective brightness values located at the wave peak portions.

By taking 110% of the minimum value of respective brightness values of the wave trough portions of the brightness curve as the minimum brightness value and taking 90% of the maximum value of respective brightness values of the wave peak portions of the brightness curve as the maximum brightness value to make certain modifications to the measured brightness values, the occurrence of extreme values may be effectively avoided thereby further increasing the test accuracy.

Optionally, using the optical measurement unit to measure the brightness of the reference object through the transparent display substrate to acquire the second brightness difference $\Delta L_2$ comprises:
using the optical measurement unit to respectively measure brightness of different portions of the black regions and brightness of different portions of the white regions through the transparent display substrate, and drawing a brightness curve according to the measured respective brightness values, as shown in FIG. 5 (see the solid line);
calculating brightness $L_W^2$ of the black regions and brightness $L_W^2$ of the white regions, wherein the brightness $L_W^2$ of the black regions is an average value of respective brightness values of wave trough portions of the brightness curve, and the brightness $L_W^2$ of the white regions is an average value of respective brightness values of wave peak portions of the brightness curve; and
calculating a difference value between the brightness $L_W^2$ of the white regions and the brightness $L_B^2$ of the black regions as the second brightness difference $\Delta L_2$ according to the equation:

$$\Delta L_2 = L_W^2 - L_B^2,$$

where $L_W^2$ is the brightness of the white regions and $L_B^2$ is the brightness of the black regions.

Furthermore, calculating the brightness of the black regions and the brightness of the white regions comprises:
in respective brightness values located at the wave trough portions of the brightness curve, taking 110% of a minimum value of the respective brightness values as a minimum brightness value, to calculate the average value of the respective brightness values located at the wave trough portions; and
in respective brightness values located at the wave peak portions of the brightness curve, taking 90% of a maximum value of the respective brightness values as a maximum brightness value, to calculate the average value of the respective brightness values located at the wave peak portions.

By taking 110% of the minimum value of respective brightness values of the wave trough portions of the brightness curve as the minimum brightness value and taking 90% of the maximum value of respective brightness values of the wave peak portions of the brightness curve as the maximum brightness value to make certain modifications to the measured brightness values, the occurrence of extreme values may be effectively avoided thereby further increasing the test accuracy.

Optionally, the optical measurement unit 22 is a brightness meter or an image sensor.

Because different regions on the reference object may be measured by means of a brightness meter or an image sensor, the result measured by using a brightness meter or an image sensor in the embodiment of the present invention may reflect the identification degree of the reference object more comprehensively, which is thereby advantageous for determining the transparency effect of the transparent display substrate more accurately. The optical measurement unit 22 may be a brightness meter or an image sensor, or may be any other brightness measurement instrument which can reflect the identification degree of the reference object comprehensively.

Optionally, distance between the optical measurement unit 22 and the reference object 23 is fixed.

Because the distance between the optical measurement unit and the reference object may influence the identification degree of the reference object measured by using the optical measurement unit, in order to test the transparency effect of the transparent display substrate more accurately, the distance between the optical measurement unit and the reference object may be fixed. After the optical measurement unit is used to directly measure the brightness of the reference object, the transparent display substrate may be placed between the optical measurement unit and the reference object, and the identification degree of the reference object may be measured through the transparent display substrate, thereby preventing the measurement result from being influenced by unfixed distance between the optical measurement unit and the reference object, which is advantageous for accurately determining the influence of the transparent display substrate on the identification degree of the reference object, thereby testing the transparency effect of the transparent display substrate more accurately.

Optionally, the device further comprises a light source 24. Because the test of transparency of a transparent display substrate needs to be performed under a certain illumination condition, and stable and continuous illumination may be provided for the test process by means of the light source 24, the influence of natural light on the test result may be decreased, which is advantageous for increasing the test accuracy of the transparency effect.

Optionally, the light source 24 is a standard light source. In addition, the light source may also be an ordinary light source. However, relative to an ordinary light source, a standard light source generally complies with international standards, and the illumination it provides is more stable and easier for adjustment. Therefore, a standard light source (e.g., a D65 standard light source) is generally selected as the light source 24.

Optionally, the distance and angle between the light source 24 and the reference object 23 are both fixed. Because the distance and angle between the light source 24 and the reference object 23 may both influence the illuminance on the surface of the reference object, thereby influencing the identification degree of the reference object measured by using the optical measurement unit, the distance and angle between the light source and the reference object may both be fixed, so as to prevent the measurement result from being influenced by the distance and angle between the light source and the reference object. This is advantageous for accurately determining the influence of the transparent display substrate on the identification degree of the reference object, thereby testing the transparency effect of the transparent display substrate more accurately.

Optionally, illuminance on the standard color plate is fixed. When the illuminance on the standard color plate is fixed, comparison and determination of transparency effects of different transparent display substrates can be facilitated.

Figure 6:
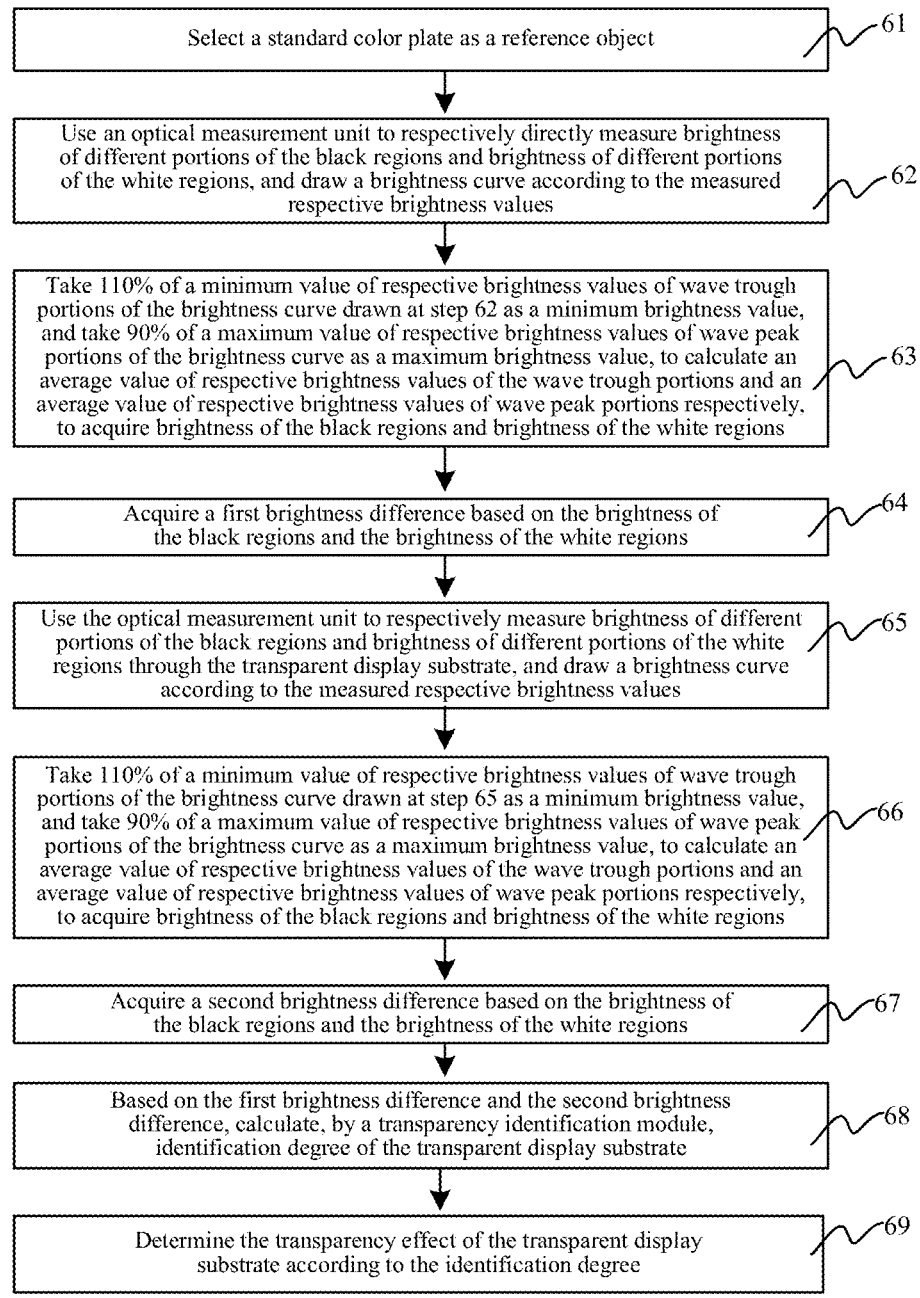
FIG. 6 is a flow chart of a method for testing transparency effect of a transparent display substrate according to the fourth embodiment of the present invention.

The fourth embodiment of the present invention provides a method for testing transparency effect of a transparent display substrate by using the device according to the second embodiment of the present invention. With reference to FIG. 6, the method comprises:

step 61 of selecting a standard color plate as a reference object;

step 62 of using an optical measurement unit to respectively directly measure brightness of different portions of the black regions and brightness of different portions of the white regions, and drawing a brightness curve according to the measured respective brightness values;

step 63 of taking 110% of a minimum value of respective brightness values of wave trough portions of the brightness curve drawn at step 62 as a minimum brightness value, and taking 90% of a maximum value of respective brightness values of wave peak portions of the brightness curve as a maximum brightness value, to calculate an average value of respective brightness values of the wave trough portions and an average value of respective brightness values of wave peak portions respectively, to acquire brightness $L_B^1$ of the black regions and brightness $L_W^1$ of the white regions;

step 64 of acquiring the first brightness difference $\Delta L_1$ based on the brightness $L_B^1$ of the black regions and the brightness $L_W^1$ of the white regions according to the equation $\Delta L_1 = L_W^1 - L_B^1$;

step 65 of using the optical measurement unit to respectively measure brightness of different portions of the black regions and brightness of different portions of the white regions through the transparent display substrate, and drawing a brightness curve according to the measured respective brightness values;

step 66 of taking 110% of a minimum value of respective brightness values of wave trough portions of the brightness curve drawn at step 65 as a minimum brightness value, and take 90% of a maximum value of respective brightness values of wave peak portions of the brightness curve as a maximum brightness value, to calculate an average value of respective brightness values of the wave trough portions and an average value of respective brightness values of wave peak portions respectively, to acquire brightness $L_B^2$ of the black regions and brightness $L_W^2$ of the white regions;

step 67 of acquiring a second brightness difference $\Delta L_2$ based on the brightness $L_B^2$ of the black regions and the brightness $L_W^2$ of the white regions according to the equation $\Delta L_2 = L_W^2 - L_B^2$;

step 68 of calculating, by a transparency identification module, identification degree ID of the transparent display substrate, based on the first brightness difference $\Delta L_1$ and the second brightness difference $\Delta L_2$ according to the equation:

$$ID = \frac{\Delta L_2}{\Delta L_1} \times 100\%;$$

and step 69 of determining the transparency effect of the transparent display substrate according to the identification degree ID. Specifically, the higher the identification degree ID is, the better the transparency effect is.

To sum up, embodiments of the present invention provide a device and a method for testing transparency effect of a transparent display substrate. The device comprises: a transparency identification module, an optical measurement unit and a reference object. When the device is used to test the transparency of the transparent display substrate, the first brightness difference may be directly acquired by means of the optical measurement unit and the reference object, and the brightness of the reference object may be measured through the transparent display substrate to acquire the second brightness difference. The identification degree of the reference object may be calculated according to the first brightness difference and the second brightness difference. Because the transparency effect of the transparent display substrate has a direct influence on whether an object behind the transparent display substrate can be clearly seen through the transparent display substrate, and the identification degree of the object is an important factor for measuring whether the object behind the transparent display substrate can be clearly seen, the transparency effect of the transparent display substrate may be determined by measuring the influence of the transparent display substrate on the identification degree of the reference object, thereby achieving the objective of testing the transparency effect of the transparent display substrate, which is advantageous for testing the transparent display substrate. Furthermore, because the influences of ambient light on different portions of the reference object are the same, acquiring the identification degree by means of the brightness differences may eliminate the influence of ambient light on the test and increase the test accuracy of the transparent display substrate.

The embodiments described above are merely exemplary embodiments of the present invention, but are not used to limit the protection scope of the present invention. The protection scope of the present invention should be defined by the appended claims.

The present application claims the priority of Chinese patent application No. 201510254560.4, filed on May 18, 2015, the disclosure of which is hereby entirely incorporated by reference.

The invention claimed is:

1. A device for testing transparency effect of a transparent display substrate, comprising: a transparency identification module, an optical measurement unit and a reference object including two kinds of regions of different colors; the optical measurement unit being able to directly measure brightness of the two kinds of regions of different colors of the reference object to acquire a first brightness difference, and to measure brightness of the two kinds of regions of different colors of the reference object through the transparent display substrate to acquire a second brightness difference; based on the first brightness difference and the second brightness difference, the transparency identification module calculating identification degree ID of the transparent display substrate according to the equation:

$$ID = \frac{\Delta L_2}{\Delta L_1} \times 100\%,$$

where $\Delta L_1$ is the first brightness difference and $\Delta L_2$ is the second brightness difference.

2. The device according to claim 1, wherein distance between the optical measurement unit and the reference object is fixed.

3. The device according to claim 1, wherein the optical measurement unit is a brightness meter or an image sensor.

4. The device according to claim 1, wherein the reference object is a standard color plate comprising black regions spaced from each other and white regions spaced from each other.

5. The device according to claim 4, wherein
when the optical measurement unit directly measures the brightness of the reference object, the difference value between the brightness of the white regions and the brightness of the black regions is the first brightness difference $\Delta L_1$; and
when the optical measurement unit measures the brightness of the reference object through the transparent display substrate, the difference value between the brightness of the white regions and the brightness of the black regions is the second brightness difference $\Delta L_2$.

6. The device according to claim 1, wherein the device further comprises a light source, and the distance and angle between the light source and the reference object are both fixed.

7. The device according to claim 6, wherein when the brightness of the reference object is measured through the transparent display substrate, the light source and the reference object are located at the same side of the transparent display substrate.

8. A method for testing transparency effect of a transparent display substrate, comprising:
selecting a reference object including two kinds of regions of different colors;
using an optical measurement unit to directly measure brightness of the two kinds of regions of different colors of the reference object to acquire a first brightness difference $\Delta L_1$;
placing the transparent display substrate between the optical measurement unit and the reference object, and using the optical measurement unit to measure brightness of the two kinds of regions of different colors of the reference object through the transparent display substrate to acquire a second brightness difference $\Delta L_2$;
based on the first brightness difference $\Delta L_1$ and the second brightness difference $\Delta L_2$, calculating identification degree ID of the transparent display substrate by a transparency identification module according to the equation:

$$ID = \frac{\Delta L_2}{\Delta L_1} \times 100\%;$$

and
determining the transparency effect of the transparent display substrate according to the identification degree ID.

9. The method according to claim 8, wherein the reference object is a standard color plate comprising black regions spaced from each other and white regions spaced from each other.

10. The method according to claim 9, wherein
when the optical measurement unit directly measures the brightness of the reference object, the difference value between the brightness of the white regions and the brightness of the black regions is the first brightness difference $\Delta L_1$; and
when the optical measurement unit measures the brightness of the reference object through the transparent display substrate, the difference value between the brightness of the white regions and the brightness of the black regions is the second brightness difference $\Delta L_2$.

11. The method according to claim 9, wherein using the optical measurement unit to directly measure the reference object to acquire the first brightness difference $\Delta L_1$ comprises:
respectively measuring brightness of different portions of the black regions and brightness of different portions of the white regions, and drawing a brightness curve according to the measured respective brightness values;
calculating brightness of the black regions and brightness of the white regions, the brightness of the black regions being an average value of respective brightness values of wave trough portions of the brightness curve, and the brightness of the white regions being an average value of respective brightness values of wave peak portions of the brightness curve; and
calculating a difference value between the brightness of the white regions and the brightness of the black regions as the first brightness difference $\Delta L_1$.

12. The method according to claim 11, wherein calculating the brightness of the black regions and the brightness of the white regions comprises:
in respective brightness values located at the wave trough portions of the brightness curve, taking 110% of a minimum value of the respective brightness values as a minimum brightness value, to calculate the average value of the respective brightness values located at the wave trough portions; and
in respective brightness values located at the wave peak portions of the brightness curve, taking 90% of a maximum value of the respective brightness values as a maximum brightness value, to calculate the average value of the respective brightness values located at the wave peak portions.

13. The method according to claim 9, wherein using the optical measurement unit to measure the brightness of the two kinds of regions of different colors of the reference object through the transparent display substrate to acquire the second brightness difference $\Delta L_2$ comprises:
using the optical measurement unit to respectively measure brightness of different portions of the black regions and brightness of different portions of the white regions through the transparent display substrate, and drawing a brightness curve according to the measured respective brightness values;
calculating brightness of the black regions and brightness of the white regions, the brightness of the black regions being an average value of respective brightness values of wave trough portions of the brightness curve, and the brightness of the white regions being an average value of respective brightness values of wave peak portions of the brightness curve; and
calculating a difference value between the brightness of the white regions and the brightness of the black regions as the second brightness difference $\Delta L_2$.

14. The method according to claim 13, wherein calculating the brightness of the black regions and the brightness of the white regions comprises:
in respective brightness values located at the wave trough portions of the brightness curve, taking 110% of a minimum value of the respective brightness values as a minimum brightness value, to calculate the average value of the respective brightness values located at the wave trough portions; and
in respective brightness values located at the wave peak portions of the brightness curve, taking 90% of a maximum value of the respective brightness values as a maximum brightness value, to calculate the average value of the respective brightness values located at the wave peak portions.

15. The device according to claim 2, wherein the optical measurement unit is a brightness meter or an image sensor.

16. The device according to claim 2, wherein the reference object is a standard color plate comprising black regions spaced from each other and white regions spaced from each other.

17. The device according to claim 3, wherein the reference object is a standard color plate comprising black regions spaced from each other and white regions spaced from each other.

18. The device according to claim 2, wherein the device further comprises a light source, and the distance and angle between the light source and the reference object are both fixed.

19. The device according to claim 3, wherein the device further comprises a light source, and the distance and angle between the light source and the reference object are both fixed.

20. The device according to claim 4, wherein the device further comprises a light source, and the distance and angle between the light source and the reference object are both fixed.

* * * * *